United States Patent [19]

Abe et al.

[11] Patent Number: 4,740,047
[45] Date of Patent: Apr. 26, 1988

[54] FIBER FOR LATERAL BEAMING OF LASER BEAM

[75] Inventors: Koichi Abe, Hitachi; Toshio Suzuki, Chiyoda; Hideyuki Takashima, Hitachi; Daijyo Hashimoto, Bunkyo; Masane Suzuki, Omiya; Motonori Kanaya, Omiya; Hiroshi Sibamoto, Omiya, all of Japan

[73] Assignees: Hatachi Cable, Ltd., Tokyo; Fuji Photo Optical Co., Ltd., Saitama; Daijyo Hashimoto, Tokyo, all of Japan

[21] Appl. No.: 841,422

[22] Filed: Mar. 19, 1986

[30] Foreign Application Priority Data

Mar. 26, 1985 [JP] Japan .................................. 60-61267

[51] Int. Cl.$^4$ .................................................. G02B 6/26
[52] U.S. Cl. ............................... 350/96.15; 350/96.10; 350/96.24; 128/1.4
[58] Field of Search ............... 350/96.10, 96.15, 96.24, 350/96.25, 96.26; 128/1.4, 5, 6

[56] References Cited

U.S. PATENT DOCUMENTS

| 2,797,683 | 7/1957 | Aiken | 128/6 |
| 4,224,929 | 9/1980 | Furihata | 128/5 |
| 4,567,882 | 2/1986 | Heller | 128/6 X |
| 4,576,147 | 3/1986 | Hashiguchi | 350/96.26 X |

FOREIGN PATENT DOCUMENTS 61-64242  4/1986  Japan.

Primary Examiner—Akm E. Ullah
Attorney, Agent, or Firm—Parkhurst & Oliff

[57] ABSTRACT

A fiber for lateral beaming of a laser beam, wherein an affected portion in a cavity of an internal organ in a living body is irradiated by the laser beam in a through-endoscopic manner. The fiber for lateral beaming of the laser beam is constructed such that a transparent tubular member is coupled to the forward end portion of a fiber through two coating layers, and an anti-reflection coating layer is formed on a laser beam exiting surface of the transparent tubular member. Owing to the anti-reflection coating layer, this fiber for lateral beaming is free from the harmful leaking beam. Since the transparent tubular member is connected to the fiber through the two coating layes, the fiber can avoid being broken.

6 Claims, 3 Drawing Sheets

FIBER FOR LATERAL BEAMING OF LASER BEAM

BACKGROUND OF THE INVENTION

This invention relates to a fiber for lateral beaming of a laser beam, and more particularly to a fiber for lateral beaming of a laser beam wherein an affected portion in a cavity of an internal organ in a living body is irradiated sideways by the laser beam in a through-endoscopic manner.

The techniques of medical treatment for conducting diagnosis and treatment of an affected portion such as a tumor in a cavity of an internal organ in a living body by laser beam irradiation in a through-endoscopic manner have been clinically put into practice by rapid progress in laser techniques and the technique of the light transmitting fiber. The fibers for introducing the laser beam into a cavity in an internal organ in a living body to irradiate the affected portion include a fiber for front beaming having a distal end face perpendicularly intersecting the longitudinal direction of the fiber, and a fiber for lateral beaming exiting at a right angle through the side surface of the fiber. When an affected portion in a narrow cavity in an internal organ such as a gullet, a trachea or a bowel is irradiated by the laser beam, it is preferable that the irradiation energy received by the affected portion be uniform on the affected portion as a whole. For this purpose, a fiber for lateral beaming for irradiating in a direction perpendicular to the wall of the cavity, i.e. for frontally irradiating the affected portion, has been proposed in Japanese Application No. 187782/1984 by the present applicant. The fiber for lateral beaming disclosed in this Patent Application No. 187782/1984 is constructed such that a distal end is formed to provide a surface inclined at about 45° to the center line of the fiber. Further, this inclined surface is formed by coupling thereto a transparent tubular member blocked at one end thereof in a manner not to include an acute angle portion, and air layer is formed behind the inclined surface of the distal end of the fiber to obtain an entirely reflecting surface, whereby the laser beam transmitted through the fiber is refracted in a direction perpendicular to the longitudinal direction of the fiber, so that the laser beam exits from the side surface of the fiber.

To explain in further detail, FIG. 6 shows a sectional view illustrating the above-discussed fiber for lateral beaming of the laser beam, wherein a fiber 11 is a light-transmitting fiber made of glass or plastics and constituted by a core and a clad which are different in refractive index from each other. In this case, the fiber is a quartz fiber having a core diameter of 400 μm and an outer clad layer diameter of 650 μm. A primary coating layer 12 made of a synthetic resin material is formed on the fiber 11 over the total length thereof. The fiber 11 formed thereon with the primary coating layer 12 is further protected by a flexible, protective outer covering jacket 13, whereby the fiber 11 is prevented from being cracked and broken. Synthetic resin materials such as vinyl resin material, nylon and Teflon are prefearbly used to form this protective outer covering jacket 13.

To refract and exit the laser beam transmitted in a direction perpendicularly intersecting the longitudinal direction of the fiber, a distal end of the fiber 11 is formed to provide a flat surface 14 inclined at about 45° to the center line of the fiber 11, and this flat surface is polished into an optically smooth surface. Portions of the primary coating layer 12 and protective outer covering jacket 13 are removed from a portion of the fiber 11, including the distal end which is formed into the flat surface 14 inclined at about 45° to the center line of the fiber as described above. The side of the distal end of the fiber 11, from which the primary coating layer 12 and protective outer covering jacket 13 are removed, is coupled to a transparent tubular member 15 of circular cross section. One end of tubular member 15 is blocked in a semispherical shape, and the distal end and the tubular member 15 are firmly attached to each other in an air-tight manner by an epoxy adhesive 30. The inclined flat surface 14 of the fiber 11 is disposed in this transparent tubular member 15 such that an air layer 32 is formed between the inner surface of the tubular member 15 and the inclined flat surface 14 of the fiber 11. A stepped portion 18 is formed at the side of the open end of the transparent tubular member 15 over the entire circumference thereof. The forward end portion of a reinforcing tube 19, made of a flexible material such as Teflon for protecting and reinforcing the fiber 11 substantially over the total length thereof, is solidly secured to this stepped portion by adhesive bonding, or by being enlarged in diameter due to heating and coupled onto the stepped portion, and thereafter cooled for shrinkage. This reinforcing tube 19 is provided with an inner diameter sufficient for forming a hollow space 21 which is annular in cross section and extends between the inner peripheral surface thereof and the protective outer covering jacket 13 of the fiber 11 over the total length, and with an outer shape substantially equal to the outer shape of the transparent tubular member 15. A groove 20, communicated with the hollow space 21 when the distal end of the fiber 11 and forward end portion of the reinforcing tube 19 are coupled to the open end of the transparent tubular member 15, is formed in a portion of the transparent tubular member 15.

The fiber for lateral beaming discussed above functions very effectively when it is used together with a front-view type endoscope in a through-endoscope manner. However, the following disadvantages have been presented by this fiber for lateral beaming.

Firstly, a thin air layer is formed between the inner wall surface of the transparent tubular member in the longitudinal direction thereof and the outer peripheral wall of the fiber, and the interface therebetween functions as a reflecting surface due to the presence of this air layer. As a result, a leaking beam is generated which is emitted in a direction other than aan aimed direction, particularly to a direction opposite to the aimed direction (namely in the direction of leaking). As the amount of energy thereof increases, this leaking beam results in burning a normal portion other than the aimed affected protion. To eliminate the interface reflection caused by the above-described air layer, it may be proposed to improve manufacturing accuracies of the outer diameter of the fiber and the inner diameter of the tubular member to obtain very high coupling accuracy, so that no air layer can remain between the members. However, the above proposal is not desirable from the viewpoint of suitability for mass production. Even if such a proposal is possible, it brings about very inefficient results in inserting the fiber, made of quartz or the like, and having a sharp forward end inclined at about 45°, straight into the tubular member without impinging against the tubular member, thus contributing to increased costs in the assembling operations.

Secondly, another leaking beam, other than the leaking beam caused by the interface of the air layer, is generated. This leaking beam is directed in the forward direction of a probe. Although it depends upon the mode of propagation of the laser beam, which has fallen into the fiber, this beam is not reflected laterally, transmitted through the surface inclined at 45°, and directed forward because of the presence of an incident beam component, the incident angle of which becomes lower than a critical angle on the entirely reflecting surface. Similarly to the former leaking beam caused by the interface reflection, the latter leaking beam results in burning a normal portion other than the aimed affected portion.

The third problem of which the fiber for lateral beaming which has heretofore been proposed, is the problem of breakage in use. Namely, under the use conditions in a through-endoscopic manner a fiber probe is not guided rectilinearly to the aimed position in a body, rather, it is introduced to the aimed portion in the body using an endoscope tridimensionally flexed for catching the affected portion in the visual field of observation of the endoscope as a path for the insertion of the fiber probe. As the path for introducing the fiber probe for this purpose, there is utilized a forceps channel having an inner diameter of about 2 to 3 mm for introducing a forceps for the treatment. A radius of curvature of this forceps channel in an endoscope used at present is fairly small, whereby an external force in a direction crossing the axial line of the fiber is applied to the forward end portion of the fiber having no flexibility when the fiber is passed through a curved portion having such a radius of curvature as described above. Under these conditions, as seen in FIG. 6, when a strong external force directed along the axial line is applied to the tubular member and therearound, a sharing force occurs at a boundary portion between a portion of the continuous fiber, which is covered by the inflexible tubular member, and a portion of the fiber, which is covered by the flexible coating layers and the flexible outer covering layer, whereby a breakage occurs at this boundary position. As the case may be, the portion of the fiber falls down together with the tubular member and remains in the body, so that very dangerous results may be brought about.

Further, there is a problem caused by the use conditions in a through-endoscopic manner, particularly caused by the use conditions using the front-view type endoscope. Since an aiming beam and the laser beam for the irradiation treatment should be confirmed within the visual field of the endoscope, the forward end of the fiber probe should be protruded forward from the forward end of the front-view type endoscope by a value commensurate to an angle of the field of observation of the endoscope. As this forward protrusion value increases, it becomes more difficult to change the degrees of flexing of the forward end portion of the endoscope and to finely adjust the direction of irradiation. Furthermore, if the flexing control of changing the degrees of flexing of this forward end portion is not carried out carefully and properly, there may be a danger of the forward end of the fiber probe coming into contact with the wall surface of the cavity particularly in a flexed narrow cavity. The above described contact may cause foreign material, such as mucus and blood which are secreted in the body, to adhere to the fiber probe, particularly to the tubular member. Adhesion of the above-described foreign material results in absorption of the laser beam, generation of heat, and finally burning.

SUMMARY OF THE INVENTION

The present invention has been developed to obviate the above-described drawbacks and disadvantages of the conventional fiber for lateral beaming of a laser beam, and has as its object the provision of a fiber for lateral beaming of a laser beam wherein harmful leaking beams are eliminated and breakages are avoided.

Another object of the present invention is to provide a fiber for lateral beaming of a laser beam wherein, when it is used together with a front-view type endoscope, the protrusion value thereof from the forward end portion of the endoscope is minimized.

To this end, the present invention contemplates that, in the fiber for lateral beaming of a laser beam, a distal end thereof is formed into a surface inclined at about 35° to 40° to the center line of the fiber, a transparent tubular member, one end of which is blocked by a surface (preferably a semispherical surface) having no acute angle portion and the inner diameter of which is formed sufficiently larger than the outer diameter of the fiber, is coupled to a forward end portion of the fiber including the aforesaid inclined surface, an air layer is formed between this tubular member and the inclined surface at the forward end portion of the fiber, and an anti-reflection coating layer is deposited on one surface of the outer surfaces of the tubular member and a high reflecting layer is deposited on the other surface.

Further, the fiber for lateral beaming of a laser beam according to the present invention is of such an arrangement that a portion of the transparent tubular member is coupled to the fiber, partially overlapping with the protective coating layers of the fiber.

Furthermore, the fiber for lateral beaming of a laser beam according to the present invention is of such an arrangement that, a flat surface parallel to the center line of the transparent tubular member is formed on a portion of the transparent tubular member, and at least a anti-reflection coating layer is deposited on this flat surface.

In the fiber for lateral beaming of a laser beam with the above-described arrangement, the distal end is formed into the entirely reflecting surface having the inclination of 35° to 40°, a reflection preventive layer is deposited on a portion of the outer side surface of the transparent tubular member covering the fiber, and an entirely reflecting layer is deposited on the outer side surface opposite to the former outer side surface, so that the harmful leaking beam can be prevented from being generated. The reflection preventive layer and entirely reflecting layer are deposited on flat portions of the tubular member, so that the layers function reliably.

Further, the transparent tubular member is coupled to the protective coated portion of the fiber, whereby the external force acting on the tubular member tends to be absorbed by the protective coated portion overlapping with the tubular member, so that the forward end portion of the fiber can be prevented from being broken.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Detailed description will hereunder be given of the preferred embodiment of the fiber for lateral beaming of a laser beam according to the present invention with reference to the accompanying drawings.

Figure 1:
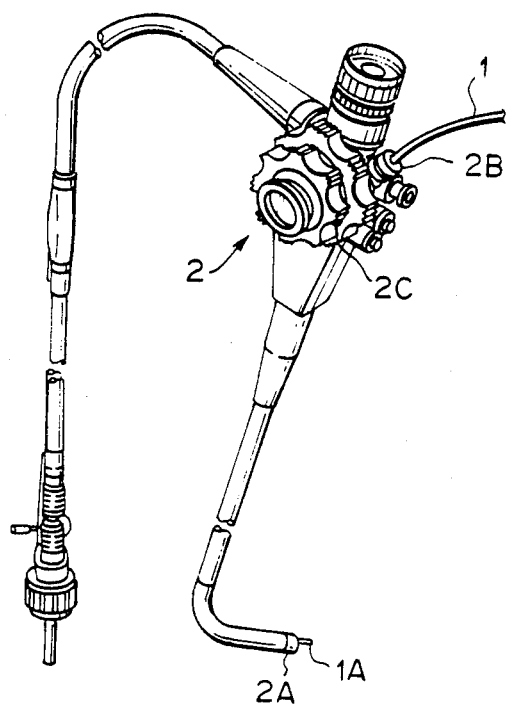
FIG. 1 is a schematic diagram showing the fiber for lateral beaming of a laser beam according to the present invention, as in the use conditions.
Figure 6:
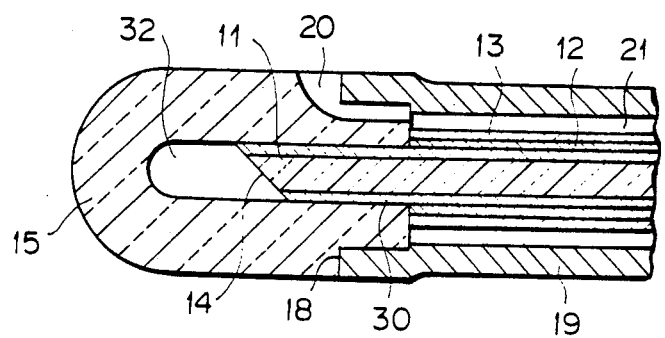
FIG. 6 is a sectional view showing the fiber for lateral beaming of a laser beam disclosed in Japanese Patent Application No. 187782/1984.

FIGS. 1 to 4 show one embodiment of the fiber for lateral beaming of a laser beam according to the present invention. As schematically shown in FIG. 1, a fiber for lateral beaming of a laser beam (hereinafter referred to as an "Irradiation probe") 1 is connected to a well-known laser beam source, not shown, and transmits a laser beam to a distal end. As well known, the irradiation probe is formed of a quartz fiber, for example, constituted by a core fiber 11 and a clad layer (Refer to FIG. 2), and the laser beam is transmitted in the probe, repeating the entire reflections. Needless to say, this irradiation probe 1 is usable as it is, however, in order to treat the cavity in an internal organ in a living body and the like without resorting to laparotomy, the irradiation probe is frequently used in a through-endoscopic manner. More specifically, an observation head 2A of an endoscope 2, well known by itself, is inserted into an aimed cavity in an internal organ, and thereafter the irradiation probe 1 is introduced into the cavity through an insertion path (as indicated by an insertion opening 2B) for an instrument for the treatment, such as a forceps, the insertion path being normally provided in the endoscope. The distal end 1A of the irradiation probe 1 together with the observation head 2A of the endoscope 2 can be adjusted in the direction of irradiation as well as the field of observation by use of a flexing adjusting knob 2C of the endoscope.

Description will hereinafter be given of the construction of the distal end 1A of this irradiation probe 1 with reference to FIGS. 2(A), 2(B), 2(C) and FIG. 3.

The fiber 11 used in the fiber for lateral beaming of a laser beam according to the present invention is made of quartz glass or plastics and is constituted by a core and a clad, which are well known and different in refractive index from each other. In the case of this embodiment, a quartz fiber is used having a core diameter of 400 μm and an outer clad layer diameter of 600 μm. The core diameter and outer clad layer diameter may be selected desirably in accordance with the purpose of use and the configuration. In the drawing, the irradiation probe 1 is provided with a triple layer construction of coating layers over the total length of the fiber. A first coating layer 12 is a so-called primary coating layer, formed of a silicone coating layer for example. A second coating jacket 13 is an outer covering jacket such as a nylon tube. A third coating layer 16 is an outer covering jacket such as a Teflon tube. The first and the second coating layers 12 and 13 are similar to those of the conventional well-known light transmitting fiber, do not directly function as the light transmitters, and rather serve to prevent the fiber 11 from being cracked and broken. The third coating layer 16 constitutes a part of the characteristics of the present invention, which will be described in detail hereinafter.

Figure 2A:
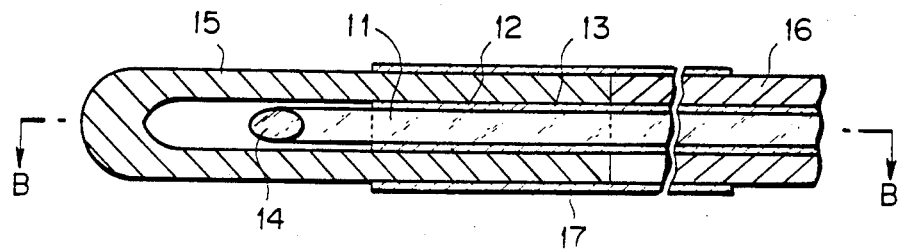
FIGS. 2(A), 2(B) and 2(C) are sectional views showing one embodiment of the fiber for lateral beaming of a laser beam according to the present invention.
Figure 2B:
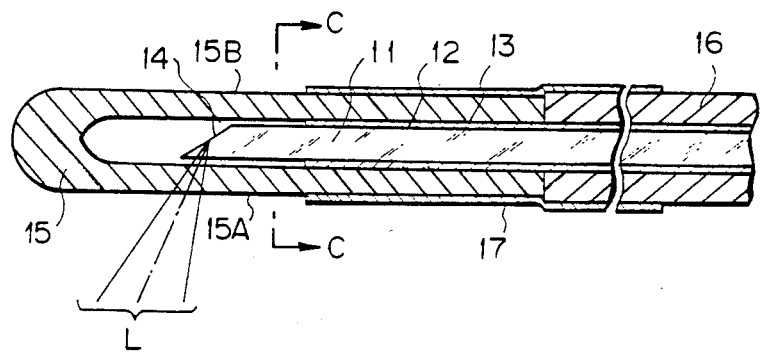
Figure 2C:
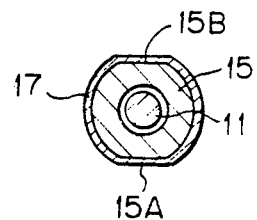
Figure 3:
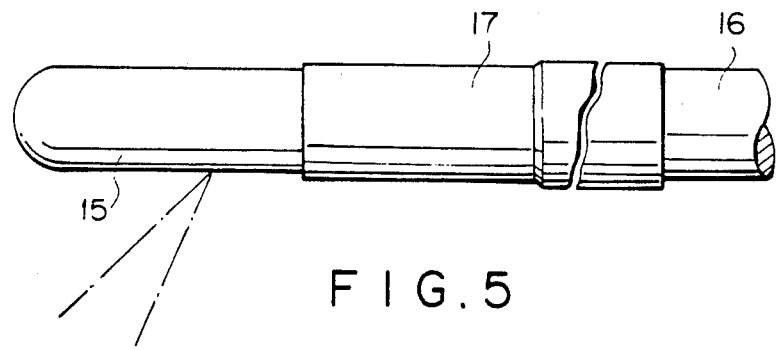
FIG. 3 shows an appearance of the fiber for lateral beaming of a laser beam shown in FIGS. 2.

The distal end of the fiber 11 is formed to provide a surface 14 inclined at about 35° to 40° to the center line of the fiber 11, and the surface 14 is polished into an optically smooth surface. In the fiber 11 formed at the distal end thereof with the inclined surface 14, the first to the third coating layers 12, 13 and 16 are removed over some length including the distal ends thereof, and the third coating layer is removed over a greater length than the other layers. A transparent, hollow tubular member 15, having one end thereof blocked in a generally semispherical shape and being circular in cross section, is coupled to an exposed portion of the second coating jacket 13, so as to incorporate therein an exposed portion of the fiber 11. An open end of the hollow tubular member 15 is closely attached to the forward end of the third coating layer 16. Contact portions between these coatings and the tubular member may preferably be joined to each other by an adhesive or the like. As shown in FIG. 2(C), the tubular member 15 is formed with flat surfaces 15A and 15B, which are opposed and substantially parallel to each other. Consequently, the coating layer 16 and the tubular member 15 are substantially equal in outer diameter to each other, however, there is a slight difference in diameter at the flat surfaces 15A and 15B between the coating layer 16 and the tubular member 15. A heat-shrinkable tube 17 is coupled onto the tubular member 15 and the third coating 16 in a manner to cover these members, and clampingly protects these members by the heat shrinking action. There is the difference in diameter at the flat surfaces 15A and 15B between these members, however, these portions are closely clamped to each other by the shrinking action of the heat shrinkable tube 17.

A reflection preventive coating layer is deposited on the flat surface portion 15A of the tubular member 15, and a highly reflective coating layer is deposited on the flat surface portion 15B.

When the irradiation probe according to the present invention with the above-described arrangement is connected to a laser unit, not shown, and a laser beam is generated, the laser beam is transmitted through the fiber 11 as well known, repeating the entire reflections entirely reflected by the inclined surface 14 transmitted through the transparent tubular member 15 including the flat surface 15A, and the irradiation of the laser beam L is carried out forward in a direction of about 60° to 75°. On the flat surface 15A, a reflected beam is prevented from being generated by the reflection preventive coating layer deposited on the flat surface 15A. A beam reflected by another interface is prevented from being transmitted by the action of the highly reflective coating layer deposited on the flat surface 15B.

In the irradiation probe 1 with the above-described arrangement, a reflected beam generated at an interface due to the presence of an air layer in the tubular member is prevented from becoming an unnecessary leaking beam and exiting in a direction other than an aimed direction by the entirely reflecting coating layer deposited on the flat surface portion 15B. Although this leaking beam cannot be completely eliminated, the leaking beam can be reduced to an extent where the thermal destruction of the normal portion can be medically, completely prevented. Consequently, it is permissible that an air layer remains between the inner surface of the tubular member 15 and the outer surface of the fiber 11. Furthermore, this makes it very easy to mount the tubular member 15 to the fiber. More specifically, it becomes unnecessary to improve the coupling accuracy between the tubular member 15 and the fiber and to perform the accuracy control strictly. Further, a difference in dimension between the inner diameter and the outer diameter is substantially equal to thicknesses of the first and the second coating layers, so that the forward end of the fiber 11 can be easily inserted into the tubular member 15, without the former impinging against the latter, thus improving the working efficiency.

Subsequently, in the joined portion between the tubular member 15 and the fiber 11, the tubular member 15 is not directly joined to the fiber 11 but is joined through the first and the second coating layers 12 and 13, so that even when a strong external force acts on the tubular member 15, the force is not applied to the fiber as a shearing force directly acting on the fiber. Consequently, breakages of the forward end of the fiber 11 can be avoided.

Figure 4A:
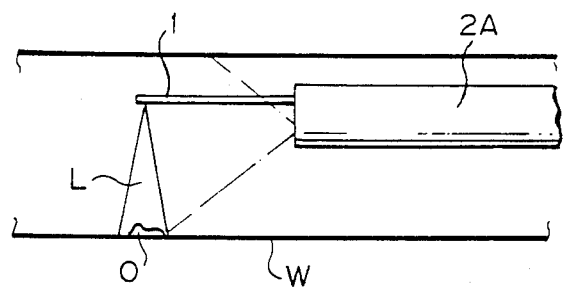
FIGS. 4(A) and 4(B) show the comparison of the protruded lengths of the forward ends of the conventional fiber for lateral beaming of a laser beam and of the fiber according to the present invention.
Figure 4B:
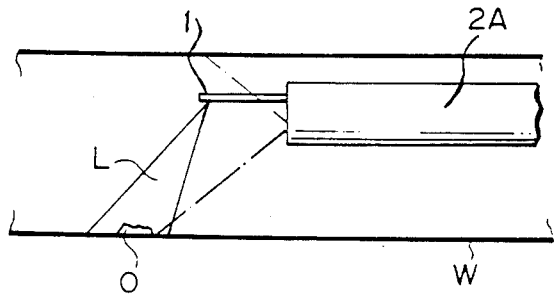

Furthermore, the direction of irradiation becomes the forward direction of about 60° to 75° to the center line of the fiber 11, whereby, as apparent from FIG. 4, the protrusion value of the irradiation probe 1 from the forward end of the endoscope is smaller as compared with one for lateral beaming at 90° (refer to FIG. 4(A)). In this case, it is conceivable that, depending on the configuration of the affected portion (as indicated by O), a shadowy portion relative to the irradiation beam L may occur. However, in that case, when the endoscope itself is inserted deeper and the observation head 2A of the endoscope is slightly curved, the same action as in the case of side irradiation at 90° can be performed. Additionally, in FIG. 4, designated at W is a wall surface of a cavity or the like.

In the above embodiment, the side surface of the exiting side of the tubular member 15 and the surface opposed thereto have been formed to provide the flat surfaces 15A and 15B, respectively. However, when the leaking beam is small in value, the flat surface 15B is dispensed with and the curved surface as is may be deposited with the highly reflective coating layer. Further, even the highly reflective coating layer may be dispensed with. As for the exiting side of the irradiation beam, the flat surface 15A may be dispensed with as the case may be; however, the anti-reflection coating layer is indispensable. However, as viewed from the characteristics of the coating layer, it is all right when a uniform layer can be deposited on the curved surface. However, in general when a layer is formed on a curved surface by the deposition method, the layer thickness is reduced from the center to the sides, whereby the portion which has the function as designed is limited to a very small scope about the center. Consequently, when the flat surface 15A is formed, the layer as designed is obtainable over the entire flat surface.

The flat surface 15A formed for the above-described purpose is advantageous in specifying a position relative to the inclined surface 14 of the fiber 11 for the assembling operation of the irradiation probe. More specifically, it is very difficult to couple onto the fiber the tubular member having a length of about 9 mm and an outer diameter of about 2 mm and not having a flat surface with a coating layer deposited thereon in such a manner that the coating layer portion of the tubular member, which is difficult to discriminate visually, is made to coincide with the exiting direction of the fiber. However, the provision of the flat surface gives the clear positional relationship therebetween, thereby facilitating assembly.

Figure 5:
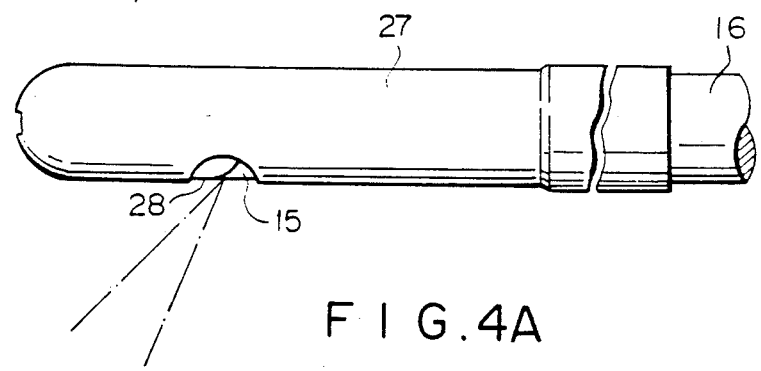
FIG. 5 shows an appearance of another embodiment of the fiber for lateral beaming of a laser beam according to the present invention.

FIG. 5 shows another embodiment of the present invention. A difference between this embodiment and the first embodiment resides in the shape of the heat-shrinkable tube, and this embodiment is identical with the first embodiment in all other respects.

In FIG. 5, the heat-shrinkable tube 27 is provided at a portion thereof corresponding to the beam exiting portion of the tubular member 15 with a circular opening 28, and covers the tubular member 15 as a whole. The function of the heat-shrinkable tube 27 in this embodiment resides in that, when the tubular member 15 is damaged for some reason or other, broken pieces are left in the heat-shrinkable tube 27 and do not remain in the body, so that the broken pieces can be taken out of the body at once.

The fiber for lateral beaming of a laser beam according to the present invention features that the laser beam is introduced into a cavity in an internal organ in a living body in a through-endoscopic manner to generally frontally irradiate an affected portion, the fiber is not broken in spite of the fact that the fiber is inserted through an introducing path of an endoscope which is very thin and has a small radius of permissible flexing, and the leaking beams of the laser beam can be reduced as much as possible, so that damage to the normal portions can be avoided.

It should be understood, however, that there is no intention to limit the invention to the specific forms disclosed. On the contrary, the invention is to cover all modifications, alternate constructions and equivalents falling within the spirit and scope of the invention as expressed in the appended claims.

What is claimed is:

1. A fiber for lateral beaming of a laser beam, comprising:
 a highly reflective surface, inclined at 35° to 40° to the center line of the fiber, formed at a distal end of the fiber; and
 a transparent first tubular member, one end of which is closed and the other end of which is coupled by means of a second tubular member to one end of the fiber having said inclined surface to form an air layer adjacent to said inclined surface;
 wherein an anti-reflection coating layer is deposited on a laser beam exiting surface of said transparent first tubular member, and further wherein two coating layers exist between said fiber and said transparent first tubular member.

2. A fiber for lateral beaming of a laser beam as set forth in claim 1, wherein said anti-reflection coating layer is deposited on a flat surface portion formed on said transparent first tubular member.

3. A fiber for lateral beaming of a laser beam as set forth in claim 1, wherein said second tubular member includes an opening for exiting the laser beam and incorporates substantially the entire transparent first tubular member.

4. A fiber for lateral beaming of a laser beam as set forth in claim 2, wherein, on said transparent first tubular member, a surface substantially symmetrical about the center line with the surface formed thereon with the anti-reflection coating layer has a highly reflective layer deposited thereon.

5. A fiber for lateral beaming of a laser beam as set forth in claim 2, wherein said fiber is provided with a third coating layer which abuts against an opening portion of said transparent first tubular member and is substantially equal in outer diameter to said transparent first tubular member.

6. A fiber for lateral beaming of a laser beam as set forth in claim 5, wherein said second tubular member is a heat-shrinkable tube.

* * * * *